United States Patent [19]
Martinelli et al.

[11] Patent Number: 6,020,512
[45] Date of Patent: Feb. 1, 2000

[54] PROCESS AND NOVEL INTERMEDIATES

[75] Inventors: Michael J. Martinelli, Zionsville; Eric D Moher, Indianapolis, both of Ind.; Naresh K Nayyar, San Diego, Calif.; Joseph M Pawlak, Southport, Ind.; David W Hoard, Greenwood, Ind.; Vien V Khau, Carmel, Ind.; John E Toth; David L Varie, both of Indianapolis, Ind.

[73] Assignees: Eli Lilly and Company, Indianapolis, Ind.; Wayne State University, Detroit, Mich.; University of Hawaii, Honolulu, Hi.

[21] Appl. No.: 09/029,189

[22] PCT Filed: Sep. 5, 1997

[86] PCT No.: PCT/US97/15669

§ 371 Date: Feb. 25, 1998

§ 102(e) Date: Feb. 25, 1998

[87] PCT Pub. No.: WO97/07798

PCT Pub. Date: Mar. 6, 1997

Related U.S. Application Data

[60] Provisional application No. 60/025,522, Sep. 6, 1996.

[51] Int. Cl.$^7$ .............................. C07C 309/72; C07F 7/08
[52] U.S. Cl. .......................... 556/417; 549/529; 556/428; 558/51
[58] Field of Search ............................ 549/529; 556/417, 556/428; 558/51

[56] References Cited

FOREIGN PATENT DOCUMENTS

WO 97/07798  3/1997  WIPO .

OTHER PUBLICATIONS

Barrow, et al. *J.Am.Chem. Soc.* 1995, 117, 2479–2490.

*Primary Examiner*—Richard L. Raymond
*Attorney, Agent, or Firm*—John H. Engelmann; William R. Boudreaux

[57] ABSTRACT

Novel processes and intermediates useful in the preparation of Cryptophycin compounds are disclosed.

11 Claims, No Drawings

PROCESS AND NOVEL INTERMEDIATES

This application is a 35 U.S.C. 371 application of PCT/US97/15669 filed on Sep. 5, 1997, which is based upon Provisional Application 60/025,522 filed Sep. 6, 1996.

This invention relates to the fields of pharmaceutical and organic chemistry and provides novel intermediates and processes useful for the preparation of cryptophycin compounds.

Antimetabolites have been used for a number of years as chemotherapeutic agents in the treatment of cancer. A new class of antimetabolites, cryptophycin compounds are useful for disrupting the microtubule system and, thus, can be useful for the treatment of cancer. In order to produce sufficient quantities of these compounds, there is a need for efficient totally synthetic processes for their preparation.

The novel processes and intermediates of this invention are important elements in providing an efficient route for preparing other cryptophycin intermediates. A special advantage provided is that the intermediates thus prepared have only minimal residual impurities. Ultimately, these intermediates can be linked to provide a total synthesis of cryptophycin compounds.

In one aspect this invention provides an intermediate of formula VIII

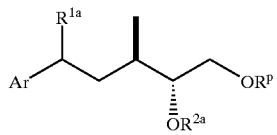

VIII wherein Ar is an aromatic, substituted aromatic, heteroaromatic or substituted heteroaromatic group;

$R^{1a}$ is halo;

$R^{2a}$ is hydrogen and or tri($C_1$–$C_6$ alkyl)silyl; and $R^P$ is $C_1$–$C_6$ alkylsulfonyl or arylsulfonyl.

This invention also relates to the compound (2R, 3R)-2-hydroxy-3-methyl-5-phenylpent-1-yl tosylate in crystalline form. Previously this compound was only available as an oil. The crystalline compound (18 infra) is a distinct advantage in obtaining purified product.

In another aspect this invention provides a process for preparing an intermediate of formula IX

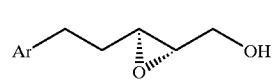

IX comprising contacting 1) L-(+)-diethyl tartrate with 2) a catalytic amount of Ti(O-i-propyl)$_4$, 3) t-butylhydroperoxide, and 4) a substrate of the formula X

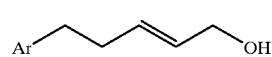

X

Additionally, this invention provides a process for preparing a compound of the formula XI

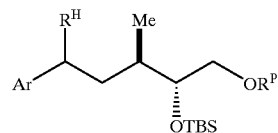

XI wherein Ar and $R^P$ are as defined supra; TBS is tert-butyldimethylsilyl; and $R^H$ is Br, Cl or I;

comprising contacting a compound of formula XII

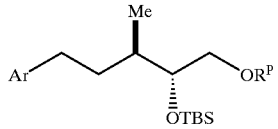

XII with N-($R^H$)succinimide and a catalytic quantity of 2,2'-azobisisobutyronitrile in a hydrocarbon or halohydrocarbon solvent.

Preferred hydrocarbon solvents are hexane and heptane. A preferred halohydrocarbon solvent is 1,2-dichloroethane. The advantages of this process are that it permits the use of an environmentally preferred solvent and it gives a cost savings. Yields are not sacrificed, and product purity is enhanced.

Further, in the process for preparing a compound of formula III

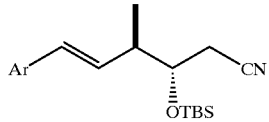

III by reacting a compound of formula II

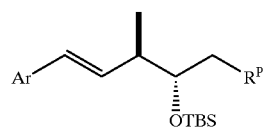

II with NaCN or KCN, this invention provides the improvement comprising adding from 0.5 to 2 equivalents of sodium bicarbonate to the reaction mixture. The bicarbonate acts as a buffer to lower the basicity of the reaction. The reaction temperature should be in the range of 60 to 90°C. This improvement results in more consistent reaction results and increased product recovery.

In yet another aspect, this invention provides a new process for epoxidizing an allylic alcohol of formula X to produce an epoxide of formula IX. This procedure replaces dichloromethane with toluene as the reaction medium for the Sharpless asymmetric epoxidation (SAE).

For example, the allylic alcohol 15 (infra) undergoes the Sharpless asymmetric epoxidation in toluene to afford 16 (infra) in high yield and enantiomeric excess. Using toluene as solvent represents a novel development where tradition calls for methylene chloride as the preferred reaction medium.

According to the known synthetic method, the Sharpless asymmetric epoxidation (SAE) is used in the preparation of cryptophycin 52 and other representative cryptophycins. The SAE involves the conversion of allylic alcohols (i.e. 15) to epoxides in high enantiopurity and yield using a novel tartrate-derived catalyst system where the oxygen transfer agent is tert-butyl hydroperoxide and the preferred reaction medium is methylene chloride. An attempt to use toluene instead of methylene chloride in the SAE has been reported for stoichiometric amounts, but useful rates were not obtained, and methylene chloride remained the solvent of choice for this transformation as well as for the catalytic SAE.

The use of toluene alone represents a significant development in terms of environmental impact minimization.

The phrase "catalytic quantity" is understood in the art. It refers to an amount that is less than a stoichiometric amount, but is sufficient to achieve the desired results.

The term "alkyl" refers to an alkyl group with the designated number of carbon atoms. It may be saturated or unsaturated, branched or straight chain. Examples of alkyl groups include methyl, ethyl, n-propyl, iso-propyl, n-butyl, propenyl, ethenyl, sec-butyl, n-pentyl, isobutyl, tert-butyl, sec-butyl, methylated butyl groups, pentyl, tert pentyl, sec-pentyl, methylated pentyl groups and the like.

The term "alkenyl" refers to an alkyl group having from one to three double bonds. "Cycloalkyl" refers to a saturated $C_3$–$C_{12}$ cycloalkyl group.

The term "aromatic group" and "heteroaromatic group" refer to common aromatic rings having 4 n+2 pi electrons in a monocyclic conjugated system or a bicyclic conjugated system. The term "aryl" refers to an aromatic group. Examples of aromatic groups are phenyl, benzyl and naphthyl. Heteroaromatic groups will contain one or more oxygen, nitrogen and/or sulfur atoms in the ring. Examples of heteroaromatic groups include furyl, pyrrolyl, thienyl, pyridyl and the like. When the aromatic or heteroaromatic groups are substituted, the substituents may be attached at any available carbon atom.

The term "halo" refers to Cl, Br, F, or I.

The processes of this invention are exemplified by Scheme I. As illustrated in the scheme, the Ar substituent is phenyl; however, other Ar groups can be used. Likewise, the illustrated halo group is Br; however, other halogens can be prepared using appropriate reagents in the processes taught herein.

Scheme I

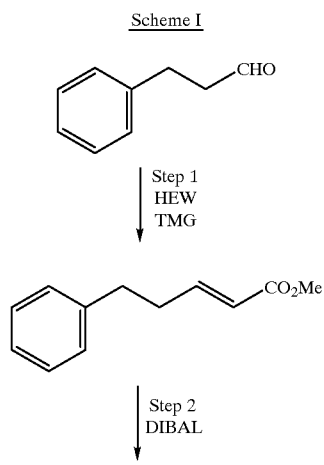

-continued

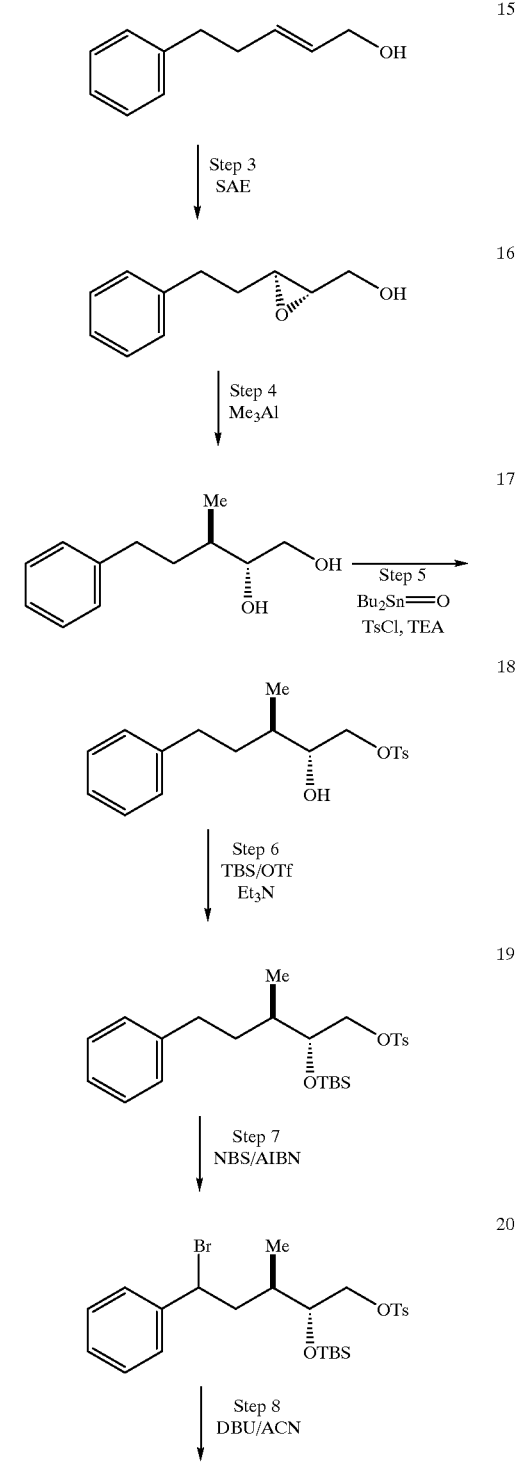

-continued

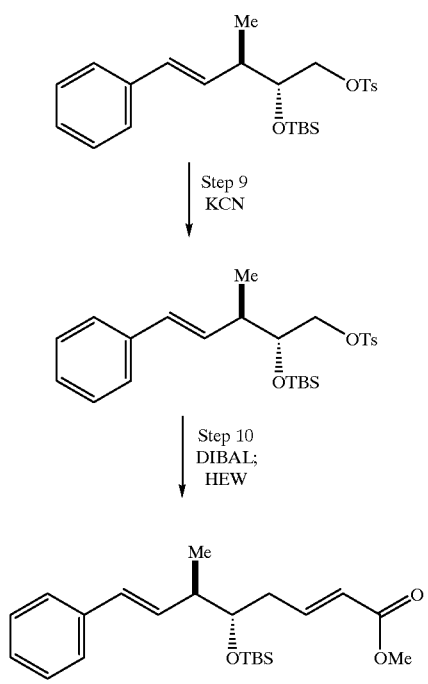

Certain abbreviations used in the Scheme include:

| | |
|---|---|
| DMAP | 4-dimethylaminopyridine |
| BOC | tert-butoxycarbonyl |
| mcpba | m-chloroperbenzoic acid |
| TMSCl | chlorotrimethylsilane |
| HEW | Horner-Emmons-Wadsworth reaction (standard reaction for olefination of an aldehyde using a phosphonate and a base) |
| TMG | 1,1,3,3-tetramethylguanidine (standard base used for the HEW reaction) |
| DIBAL | diisobutylaluminum hydride (standard reagent for the reduction of an unsaturated ester to an allylic alcohol) |
| SAE | Sharpless Asymmetric Epoxidation (established reaction for the enantioselective epoxidation of allylic alcohols) |
| TBS | tert-butyldimethylsilyl |
| TBS-OTf | TBS trifluoromethanesulfonate (standard reagent for the t-butyldimethylsilylation of alcohols) |
| AIBN | 2,2'-azobis (isobutyronitrile) (standard radical initiator) |
| ACN | acetonitrile |
| DBU | 1,8-diazabicyclo [5.4.0] undec-7-ene (standard amine base) |

The processes and intermediates of this invention provide improvements in the total synthesis of cryptophycin compounds. They enable the synthesis to be shorter and more efficient than known total sythetic methods. See Barrow, et al. *J. Am. Chem. Soc.* 1995, 117, 2479–2490.

In addition to the known cryptophycins, the term "crytophycin compound" also includes new cryptophycin compounds, such as those of formula I

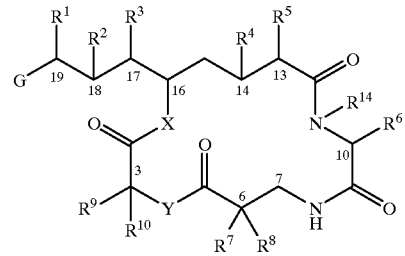

wherein

G is $C_1$–$C_{12}$ alkyl, $C_2$–$C_{12}$ alkenyl, $C_2$–$C_{12}$ alkynyl or Ar;

Ar is an aromatic or heteroaromatic group or a substituted aromatic or heteroaromatic group;

$R^1$ is halo, SR, OR, amino, mono or di-($C_1$–$C_6$-alkyl) amino, tri ($C_1$–$C_6$-alkyl) ammonium, $C_1$–$C_6$-alkylthio, di ($C_1$–$C_6$-alkyl)sulfonium, $C_1$–$C_6$-alkylsulfonyl, or $C_1$–$C_6$-alkylphosphonyl; and $R^2$ is OH or SH; or $R^1$ and $R^2$ taken together form a second bond between C-18 and C-19 or together form an epoxide, aziridine, episulfide, or cyclopropyl ring;

R is H, $C_1$–$C_6$ alkyl, $C_1$–$C_6$ alkanoyl or Ar;

$R^3$ is $C_1$–$C_6$ alkyl;

$R^4$ and $R^5$ are H; or $R^4$ and $R^5$ taken together form a second bond between C-13 and C-14;

$R^7$ is H, $C_1$–$C_6$ alkyl $NR^{51}R^{52}$, —($C_1$–$C_3$-alkyl)$NR^{51}R^{52}$, or $OR^{51}$; and $R^8$ is H or $C_1$–$C_6$ alkyl; or $R^7$ and $R^9$ together form a cyclopropyl ring;

$R^{51}$ and $R^{52}$ independently are $C_1$–$C_3$ alkyl;

$R^9$ is H, $C_1$–$C_6$ alkyl, $C_2$–$C_6$ alkenyl, $C_2$–$C_6$-alkynyl or ($C_1$–$C_6$ alkyl) $C_3$–$C_5$ cycloalkyl;

$R^{10}$ is H or $C_1$–$C_6$ alkyl; and $R^{14}$ is H or a lower alkyl group.

Appropriate starting materials and reagents can be used to prepare desired compounds using the guidance of the previous scheme and following examples. Many of the reagents are commercially available, and those which are not can be prepared using accepted chemical methods.

The necessary reaction time is related to the starting materials and operating temperature. The optimum reaction time for a given process is, as always, a compromise which is determined by considering the competing goals of throughput, which is favored by short reaction times, and maximum yield, which is favored by long reaction times.

To further illustrate the invention the following non-limiting examples are provided.

Preparation 1
Step 1. Methyl 5-phenylpent-2(E)-enoate (14)

A solution of trimethyl phosphonoacetate (376 g, 417 mL, 2.07 mol) in THF (750 mL) was stirred at 0° C. in a 3L 3-neck round- bottom flask equipped with a mechanical stirrer and $N_2$ inlet. To the chilled solution, neat 1,1,3,3-tetramethylguanidine (TMG) (239 g, 260 mL, 2.07 mol) was added dropwise via an addition funnel. The chilled clear pale yellow solution was stirred for 25 minutes at 0° C. A solution of hydrocinnamaldehyde (13) (90%, 253 g, 248 mL, 1.9 mol) in THF (125 mL) was added dropwise to the reaction solution slowly. Upon completion of addition, the reaction was stirred for 10 h rising to room temperature. GC indicated a 95:5 ratio of product to starting material. Water (500 mL) was added to the reaction vessel, and the reaction was stirred overnight, then separated into two layers. The organic layer was isolated, and the aqueous layer was extracted with t-BuOMe. The organic layers were combined and dried over $MgSO_4$, then concentrated in vacuo to yield an orange oil. The crude product was distilled at 129° C./0.3 mm Hg, yielding the title compound (360.5 g, 91.7% yield), as a clear, slightly yellow oil. EIMS m/z 190(13; M+), 159(410, 158(39), 131(90), 130(62), 117(22), 104(12), 95(57), 91(100), 77(21), 65(59); HREIMS m/z 190-0998 ($C_{12}H_{14}O_2$ D−0.4 mnu); UV λmax (e) 210 (8400), 260 (230) nm; IR vmax 3027, 2949, 1723, 1658, 1454, 1319, 1203, 978, 700 $cm^{-1}$; $^1H$ NMR δ ($CDCl_3$) 7.15–7.3 (Ph-H5;bm), 7.00 (3-H;dt, 15.6/6.6), 5.84 (2-H;dt, 15.6/1.2), 3.70 (OMe;s), 2.76 (5-H2;t, 7.2), 2.51 (4-H2; bdt, 6.6/7.2); $13_c$ NMR δ ($CDCl_3$) 166.9 (1), 148.3(3), 140.6(Ph-1'), 128.4/128.2 (Ph2'/31/5'6'), 126.1 (Ph 4'), 121.4 (2). 51.3 (OMe), 34.2/ 33.8 (4/5).

Step 2. 5-Phenyl-pent-2-en-l-ol (15)

To a 12L 4-neck round-bottom flask equipped with a thermocouple, mechanical stirrer and $N_2$ inlet, a solution of enoate ester (14) (310.5 g, 1.5 mol) in THF (1.5 L) was charged and chilled to −71° C. via an i-PrOH/$CO_2$ bath. To the reaction vessel was added dropwise DIBAL (2.5 L, 1.5 M in toluene, 3.75 mol) at a rate to maintain the reaction temperature <−50° C. Upon complete addition, the reaction was stirred overnight with the reaction temperature <−50° C. TLC (3:1 Hexanes:EtOAc, $SiO_2$) indicated absence of starting material after 16 h. The reaction temperature was allowed to raise to −15° C. The reaction was quenched slowly with1N HCl (150 mL). At this point the reaction mixture became a gelatinous semi-solid. A spatula was used to breakup this semi-solid, and 1N HCl (200 mL) was added, making the mixture more fluid. Concentrated HCl (625 mL) was charged to form a two phase system. The layers were separated, and the product extracted with t-BuOMe. The organic layer was dried over $MgSO_4$ and concentrated in vacuo to yield the title product as a clear pale yellow oil, 247.8 g. The crude product was distilled at 145° C./0.25mm Hg, yielding 209.7 g, 86.2%. EIMS m/z 162 (1:M+) 144 (16), 129 (7), 117 (9) 108 (6), 92 (17), 91 (100), 75 (5), 65 (12), HREIMS m/z 162, 1049 ($C_{11}H_{14}0$, D −0.4 mmu); UV λmax (e) 206 (9900), 260 (360); IR vmax 3356, 2924, 1603, 1496, 1454, 970, 746, 700 $cm^{-1}$; $^1H$ NMR δ7.15–7.3 (Ph-H5;m), 5.70 (3-H;dt, 15.6/6.0), 5.61 (2H;dt, 15.6/4.8), 4.02 (1-H2;d 4.8), 2.68 (5-H2; t, 7.2), 2.40 (OH;bs), 2.36(4-H2; dt, 6.0/7.2); $^{13}C$ NMR δ141.6 (Ph 1'), 131.8(3), 129.5 (2), 128.3/128.2 (Ph 2'/3'/5'/6'), 125.7 (Ph 4'), 63.3 (1), 35.4/33.8 (4/5).

EXAMPLE 1

Step 3 (2S,3S)-2,3-Epoxy-5-phenyl-l-pentanol (16).

To a 1L 3-neck round-bottom flask equipped with a mechanical stirrer, thermocouple and nitrogen inlet was added $CH_2C_{12}$ (350 mL), dried 4 Å molecular sieves (30 g) and L-(+)-diethyl tartrate (7.62 g, 0.037 mol). The resulting mixture was cooled to −20° C. and treated with Ti(O-i-Pr)$_4$ (9.2 mL, 0.031 mol), followed by the addition of t-butylhydroperoxide (4.0 M in $CH_2Cl_2$, 182 mL, 0.78 mol) at a rate to maintain the temperature ²−20° C. Upon complete addition, the reaction mixture was stirred for another 30 min, and then treated with a solution of the allylic alcohol (15) (50 g, 0.31 mol) in $CH_2C_{12}$ (30 mL) at a rate to maintain the temperature at −20° C. The reaction was stirred at the same temperature for 5 h, then filtered into a solution of ferrous sulfate heptahydrate (132 g) and tartaric acid (40 g) in water (400 mL) at 0° C. The mixture was stirred for 20 min, then transferred to a separatory funnel and extracted with t-BuOMe (2×200 mL). The combined organic phase was stirred with 30% NaOH solution containing NaCi, for 1 h at 0° C. The layers were again separated, and the aqueous phase extracted with t-BuOMe. The combined organic phase was washed with brine, dried over $MgSO_4$ and concentrated to yield the title compound (52.8 g) as an amber oil.

EXAMPLE 2

Step 4. (2R, 3R)-2-Hydroxy-3-methyl-5-phenylpentan-1-ol (17)

To a 5L 3-neck round-bottom flask equipped with a mechanical stirrer, thermocouple and nitrogen inlet was added a mixture of hexanes (IL). The vessel was cooled to 0° C. A 2.0 M solution of $Me_3Al$ in hexanes (800 mL, 1.6 mol) was added, followed by a solution of epoxide 16 (120 g, 0.677 mol) in hexanes (250 mL)/$CH_2Cl_2$ (50 mL), maintaining the temperature below 20° C. Upon complete addition, the cloudy reaction mixture was stirred at 5° C. for 35 min. Then a solution of 10% HCl (300 mL) was added dropwise, followed by the addition of conc HCl (350 mL). The layers were separated, and the organic phase was washed with brine and dried over $MgSO_4$. After removal of the volatiles in vacuo, the title compound (122.1 g) was obtained as an oil.

Step 5. (2R, 3R)-2-Hydroxy-3-methyl-5-phenylpent-1-yl Tosylate (18)

(a) To a 2L 3-neck round-bottom flask equipped with a mechanical stirrer and nitrogen inlet was added diol 17 (58 g, 0.30 mol), dibutyltin oxide (1.5 g, 0.006 mol, 2 mol %), p-toluenesulfonyl chloride (57.5 g, 0.30 mol), $CH_2Cl_2$ (580 mL) and triethylamine (42.0 mL, 0.30 mol). The resulting mixture was stirred at room temperature for 2 h (although the reaction was complete within 1 h), filtered, washed with water and dried over $MgSO_4$. Concentration of the volatiles in vacuo afforded the title compound (104.1 g) as a slightly amber oil.

(b) Compound 17, recovered as a crude oil (17 g) following a dilute HCl and water workup, was dissolved in hot ethyl acetate (1 weight volume) and hot heptane (4 weight volume). When the solution was cooled to 0° C. with stirring, a white precipitate formed. The mixture was stirred for 30–120 min. and filtered. The filtrate was washed with cold (0° C.) heptane-ethyl acetate (4:1) and vacuum dried (room temp.) to give crystalline compound 18 as a white solid (>92% pure by 500 MHz $^1H$ NMR), mp 44–47° C.

Step 6. (2R, 3R)-2-(tert-Butyldimethylsilyloxy)-3-methyl-5-phenylpent-1-yl Tosylate (19)

A solution of tosylate 18 (100 g, 0.29 mol) and triethylamine (81.0 mL, 0.58 mol) in $CH_2Cl_2$ (1200 mL) was treated with neat TBS-OTf (99 mL, 0.43 mol) dropwise with continued stirring for another 20 min. The reaction was washed twice with brine, dried over $MgSO_4$ and concentrated to dryness. The oil was dissolved in a minimal amount of hexanes and filtered over a silica pad, eluting with hexanes:EtOAc (9:1) to yield the title compound as a slightly amber oil, 134 g.

Step 7. (2R, 3R,5RS)-2-(tert-Butyldimethylsilyloxy)-3-methyl-5-bromo-5-phenylpent-1-yl Tosylate (20)

To a 5L 3-neck round-bottom flask equipped with a mechanical stirrer, reflux condenser and nitrogen inlet was added $CCl_4$ (1680 mL), tosylate 19 (140 g, 0.30 mol), NBS (65 g, 0.365 mol) and AIBN (16.5 g, 0.10 mol). The mixture was degassed by evacuation under full vacuum with stirring, and backfilling with nitrogen (3×). The reaction mixture was then heated to reflux, whereupon the color became dark brown. After 15 min at vigorous reflux, the reaction mixture became light yellow, and chromatographic analysis indicated the reaction was complete. After cooling to room temperature, the reaction was filtered, and the filtrate was concentrated to dryness. The residue was redissolved in hexanes, filtered again, and concentrated to dryness to afford the title compound (170.3 g) as an amber oil.

Step 8. (2R, 3R)-2-(tert-Butyldimethylsilyloxy)-3-methyl-5-phenylpent-4(E)-en-1-yl Tosylate (21)

To a 2L 3-neck round-bottom flask equipped with a mechanical stirrer, reflux condenser and nitrogen inlet was added a solution of bromide 20(100 g, 0.186 mol) in acetonitrile (700 mL). DBU (83.6 mL, 0.557 mol) was added, and the resulting dark brown solution was stirred at reflux for 15 min. After cooling to room temperature, the solvent was removed in vacuo, and the residue digested in $CH_2Cl_2$ (200 mL) and filtered through a silica pad. The volatiles were again evaporated, and the residue dissolved in EtOAc and washed with water, brine and dried over $MgSO_4$ and concentrated to dryness. Preparative hplc (Prep 500) chromatography afforded the desired unsaturated title compound (50.3 g, 60% yield over 4 steps).

Step 9. (3S, 4R)-3-(tert-Butyldimethylsilyloxy)-4-methyl-6-phenylhex-5(E)-en-1-nitrile (22)

Tosylate 21 (50 g, 0.11 mol) was dissolved in DMSO (1 L) and treated with KCN (14.2 g, 0.22 mol) and water (25 mL). The resulting mixture was stirred at 60° C. under nitrogen for 18 h. After cooling to room temperature, the reaction mixture was partitioned between EtOAc (1 L) and water (1 L). The aqueous phase was extracted with EtOAc (500 mL), and the combined organic phase was washed with brine and dried over $Na_2SO_4$. Flash chromatography over silica with $CH_2Cl_2$ afforded the desired nitrile (22) in 92% yield.

Step 10. Methyl (5S, 6R)-5-(tert-Butyldimethylsilyloxy)-6-methyl-8-phenylocta-2(E),7(E)-dienoate (1).

Nitrile 22 (14.67 g, 46.5 mmol) was dissolved in toluene (200 mL) and cooled to −78° C. under nitrogen. A 1.5 M solution of DIBAL in toluene (37.2 mL, 55.8 mmol) was added dropwise with vigorous stirring. Upon complete addition, the cooling bath was removed, and the reaction was stirred at room temperature for 1 h. The reaction mixture was carefully poured into 1 N HCl and the mixture stirred at room temperature for 30 min. The layers were separated, and the organic phase was washed with a saturated aqueous solution of sodium potassium tartrate (2×), brine and dried over $Na_2SO_4$. The volatiles were removed in vacuo, and the crude pale yellow oil was used directly in the subsequent condensation. The crude aldehyde from above was dissolved in THF (90 mL) and treated with trimethyl phosphonoacetate (9.03 mL, 55.8 mmol) and TMG (7.0 mL, 55.8 mmol) at room temperature under nitrogen. The reaction mixture was stirred for 16 h, then partitioned between EtOAc (200 mL) and water (100 mL). The aqueous phase was back extracted with EtOAc (100 mL), and the combined organic phase was washed with water, brine and dried over $Na_2SO_4$. The volatiles were removed in vacuo, and the crude yellow oil (17.0 g) was chromatographed over silica gel with $CH_2Cl_2$: cyclohexane (1:1 to 2:1) to afford 13.67 grams of the desired ester 1, 78.5%.

EXAMPLE 3
Alternate Preparation of Compound 22

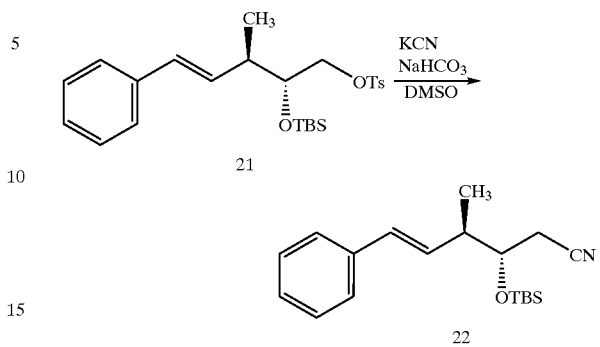

A solution of 21 (1.31 Kg, 2.84 mol) in DMSO (6.5 L) was stirred at ambient temperature as potassium cyanide (370 g, 5.68 mol) and sodium bicarbonate (240 g, 2.85 mol) were charged. The reaction was heated and stirred at 80° C. for 5 hours; then it was allowed to gradually cool to ambient temperature overnight, at which point it was complete by HPLC[1]. The reaction was quenched by adding the mixture to cold (0–10° C.) water (4 L) in one portion with agitation. Heptane (4 L) was added, and the layers were sparated. The organic layer was washed successively with water (2 L) then aqueous saturated NaCl (2 L). The organic layer was dried with silica gel 60[2] (280 g). The drying agent was filtered and rinsed with heptane (2×1 L), and the filtrate was concentrated in vacuo to give 803 g (90% yield as is) of 22 as an oil.

EXAMPLE 4
SAE in methylene chloride using one volume of toluene.

A solution of L-(+)-diethyl tartrate (766 mg, 3.70 mmol) in [1] HPLC system: Zorbax SB-C18 25 cm column, 90:10/ACN:water eluent, 220 nm, 1.0 mL/min. The reaction was considered complete when less than or equal to 3% area 21 remained. [2] Silica gel was used as the drying agent because it also removed some baseline impurities. methylene chloride (25 ml) over activated 4 Å powdered molecular sieves (3.0 g) was cooled to −20° C. and Ti(O-i-Pr)$_4$ (0.917 ml, 3.08 mmol) was added. After the mixture was stirred for 10 min, a solution of 15 (5.00 g, 30.8 mmol) in toluene (5.0 ml) was added maintaining the temperature below −18° C. The reaction was stirred at −20° C. for 35 min and tert-butyl hydroperoxide in decane (14.54 ml, 77.05 mmol, 5.3 M, stored over pellet 3 Å molecular sieves for 30 min prior to use) was added over 20 min, maintaining the temperature below −18° C. The reaction was allowed to stir at −20° C. until HPLC analysis[3] showed >98% conversion (2.5 h). The reaction was allowed to warm to −5° C. and was poured into a mixture comprised of FeSO$_4$7H$_2$O (13.2 g), tartaric acid (4.0 g), and 40 ml of water at 2° C. After stirring for 20 min the brown mixture was filtered through celite, washing with toluene. The filtrate layers were sparated and the aqueous was washed with toluene (2×20 ml). The combined organics were poured into a mixture containing NaCl (2.5 g), NaOH (15 g), and 40 ml of water at 0° C. After stirring for 1 h, the layers were separated and the aqueous layer was extracted with toluene (2×20 ml). The combined organics were dried (MgSO$_4$), filtered, and concentrated in vacuo to give a yellow oil. Chromatography (165 g of flash SiO$_2$) eluting with ethyl acetate:hexanes (2:1) provided 4.46 g (81%) of 16 as a colorless oil. 3 HPLC conditions: Chromsil C-18 column (1×25 cm), isocratic elution (50% acetonitrile/50% water both with 0.5% TFA), 1 ml/min flow rate for 20 min with UV detection ata 206 nm.

EXAMPLE 5
SAE using toluene alone

A soluton of L-(+)-diethyl tartrate (152 mg, 0.74 mmol) in toluene (6.5 ml) containing activated 4 Å powdered molecular sieves (600 mg) was cooled to −20° C. and Ti(0-i-Pr)$_4$ (0.184 ml, 0.62 mmol) was added. After the mixture was stirred for 10 min, a solution of 15 (1.00 g, 6.16 mmol) in toluene (0.5 ml) was added maintaining the temperature below −18 ° C. The reaction was stirred at −20° C. for 35 min and tert-butyl hydroperoxide in decane (2.91 ml, 15.4 mmol, 5.3 M, stored over pellet 3 Å molecular sieves for 5 min prior to use) was added over 15 min, maintaining the temperature below −18° C. The reaction was allowed to stir at −20° C. until HPLC analysis, as described in Example 4, showed >95% conversion (4.5 h). Workup as in Example 4 provided 1.56 g of a crude oil.

We claim:

1. A compound of formula VIII

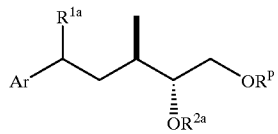

VIII wherein Ar is an aromatic, substituted aromatic, heteroaromatic or substituted heteroaromatic group;

$R^{1a}$ is halo;

$R^{2a}$ is hydrogen and or tri($C_1$–$C_6$ alkyl)silyl; and $R^P$ is $C_1$–$C_6$ alkylsulfonyl or arylsulfonyl.

2. An intermediate of claim 1 wherein Ar is substituted phenyl.
3. An intermediate of claim 1 wherein Ar is phenyl.
4. An intermediate of claim 1 wherein $R^{2a}$ is hydrogen.
5. An intermediate of claim 1 wherein $R^{1a}$ is Br.
6. In the process for preparing a compound of formula III

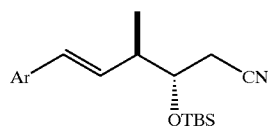

II by reacting a compound of formula II

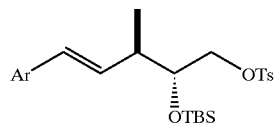

II with NaCN or KCN the improvement comprising adding from about 0.5 to about 2 equivalents of sodium bicarbonate to the reaction mixture.

7. An improvement of claim 6 wherein the reaction is with KCN.

8. An improvement of claim 6 wherein Ar is phenyl.

9. A process for preparing a compound of formula XI

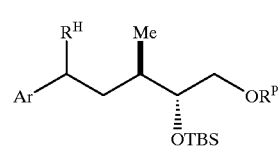

XI wherein Ar and $R^P$ are as defined in claim 1; TBS is tert-butyldimethylsilyl; and $R^H$ is Br, Cl or I;

comprising contacting a compound of formula XII

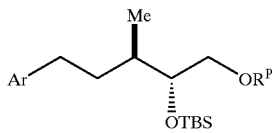

XII with N-($R^H$)succinimide and a catalytic quantity of 2,2'-azobisisobutyronitrile in a hydrocarbon or halohydrocarbon solvent.

10. A process of claim 9 wherein the solvent is heptane.
11. A process of claim 9 wherein the $R^H$ is Br.

* * * * *